United States Patent [19]

Fukui et al.

[11] 4,431,564
[45] Feb. 14, 1984

[54] LIQUID-CRYSTALLINE BIPHENYL OR TERPHENYL DERIVATIVES

[75] Inventors: Masahiro Fukui; Hiromichi Inoue; Yasuyuki Goto; Hideo Sato; Takashi Inukai, all of Kanagawaken, Japan

[73] Assignee: Chisso Corporation, Osaka, Japan

[21] Appl. No.: 369,111

[22] Filed: Apr. 16, 1982

[30] Foreign Application Priority Data

May 1, 1981 [JP]  Japan ................................... 56-66253
Sep. 8, 1981 [JP]  Japan ................................. 56-141376

[51] Int. Cl.$^3$ ........................ C09K 3/34; C07C 121/75
[52] U.S. Cl. ............................ 252/299.66; 260/465 F
[58] Field of Search ................ 260/465 F; 252/299.66

[56] References Cited

U.S. PATENT DOCUMENTS 3,947,375  3/1976  Gray et al. .......................... 252/299

*Primary Examiner*—Dolph H. Torrence

*Attorney, Agent, or Firm*—Wenderoth, Lind & Ponack

[57] ABSTRACT

New liquid crystal (l. c.) compounds having a positive dielectric anisotropy, 4''-(β-alkyloxyethyl)-4-cyanobiphenyls and 4'-(β-alkyloxyethyl)-4-cyanoterphenyls expressed by the general formula

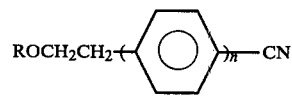

wherein R represents an alkyl group of 1~9C and n is 2 or 3; a process for preparing the same; and l.c. compositions containing at least one of the same, are provided. When the compounds are added to a l.c. having a nearly zero or negative anisotropy, a l.c. composition having a positive dielectric anisotropy can be obtained. The compounds have a greater optical anisotropy and a superior compatibility with other l.c. compounds.

6 Claims, No Drawings

LIQUID-CRYSTALLINE BIPHENYL OR TERPHENYL DERIVATIVES

BACKGROUND OF THE INVENTION

This invention relates to novel organic compounds and more particularly it relates to novel liquid-crystalline compounds having a positive dielectric anisotropy, useful as a component of liquid-crystalline materials.

As is well known, liquid-crystalline substances can be utilized for display elements (the so-called TN cell) in which a nematic liquid crystal having a twisted liquid crystal arrangement is used, and besides, they have been widely utilized for display elements in which the guest-host effect of a liquid-crystalline substance or a mixture of liquid-crystalline substances containing a suitable dyestuff is applied; DS type display elements utilizing the dynamic scattering effect of liquid crystals; display elements utilizing the cholesteric-nematic phase transition of liquid crystals; DAP type display elements utilizing the electric field-controlling birefringence effect of liquid crystals; and the like. However, none of these liquid-crystalline materials can alone endure practical uses with respect of their various characteristic properties such as liquid crystal temperature range, actuation voltage, response performance, etc., and it is the present status that practically a few liquid-crystalline compounds have been admixed to obtain materials which are endurable to uses to a certain extent.

The object of the present invention is to provide compounds useful as a component of liquid crystal compositions which are superior in such practical performances and also stable.

SUMMARY OF THE INVENTION

The present invention resides in 4'-($\beta$-alkyloxyethyl)-4-cyanobiphenyls and 4'-($\beta$-alkyloxyethyl)-4-cyanoterphenyls expressed by the general formula

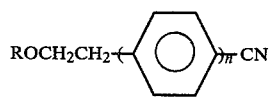

(I)

wherein R represents an alkyl group of 1 to 9 carbon atoms and n represents 2 or 3, a process for preparing the same as well as liquid crystal compositions containing at least one of the same.

DETAILED DESCRIPTION OF THE INVENTION

The compounds of the formula (I) have a positive dielectric anisotropy and when they are added to liquid crystals having a nearly zero or negative dielectric anisotropy, it is possible to obtain liquid crystal compositions having a positive dielectric anisotropy. Further, when the compounds of the formula (I) wherein n=2 are added to liquid crystals having a positive dielectric anisotropy, it is possible to reduce the threshold voltage in their electroptical response.

Further, the compounds of the formula (I) wherein n=3 are liquid-crystalline compounds which have a somewhat higher viscosity but a broader nematic range, a higher N-I point and a superior stability.

Furthermore, the compounds of the present invention have a greater optical anisotropy and also have effects of preventing color unevenness and broadening view field angle. The compounds of the present invention are superior in the compatibility with other liquid crystalline compounds; hence they can exhibit the above-mentioned various effects when they are mixed with a liquid crystal or a mixture of a few kinds of liquid crystals, e.g. liquid crystals of biphenyl group, ester group, azoxy group, cyclohexanecarboxylic acid phenyl ester group, phenylcyclohexane group, phenyl pyrimidine group, phenylmetadioxane group, etc.

The compounds of the present invention can be synthesized as follows:

First, the steps of producing the compounds of the formula (I) wherein n=2 will be illustrated by the following equations:

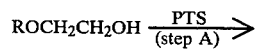

(II)

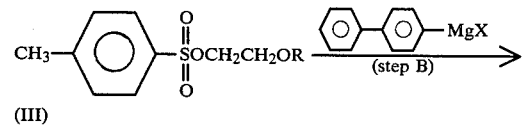

(III)

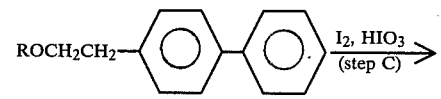

(IV)

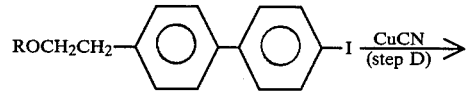

(V)

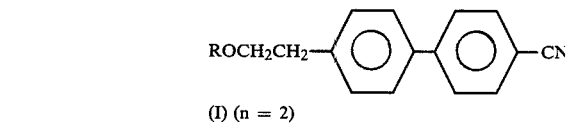

(I) (n = 2)

An ethylene glycol mono-n-alkyl ether (II) as a starting raw material is reacted with p-toluenesulfonyl chloride (PTS) in dry pyridine to obtain a p-toluenesulfonic acid $\beta$-alkyloxyethyl (III) (Step A). Then this compound (III) and p-bromobiphenyl are subjected to Grignard reaction to obtain a 4-($\beta$-alkyloxyethyl)-biphenyl (IV) (Step B). This compound (IV) is heated together with iodine and iodic acid to obtain a 4'-($\beta$-alkyloxyethyl)-4-iodobiphenyl (V) (Step C). Finally this compound (V) is reacted with cuprous cyanide to obtain an objective 4'-($\beta$-alkyloxyethyl)-4-cyanobiphenyl corresponding to the formula (I) wherein n=2 (Step D).

The compounds of the formula (I) wherein n=3 may be produced by the steps as follows:

(VI)

-continued

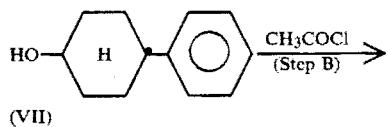
(VII)

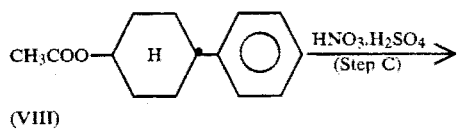
(VIII)

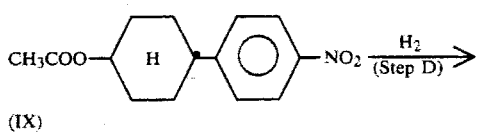
(IX)

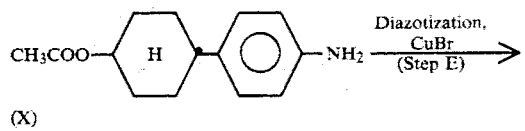
(X)

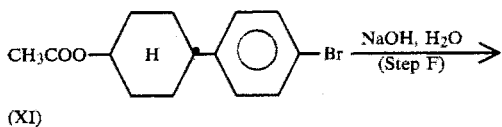
(XI)

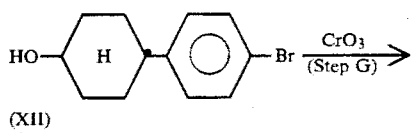
(XII)

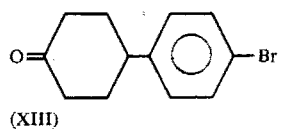
(XIII)

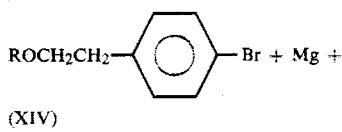
(XIV)

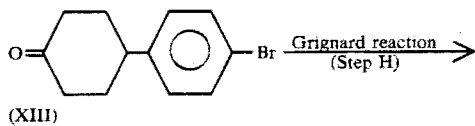
(XIII)

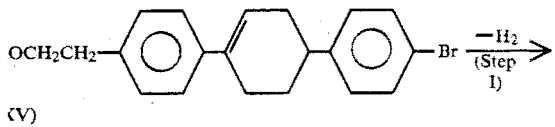
(V)

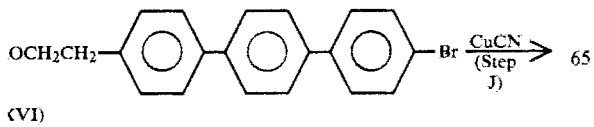
(VI)

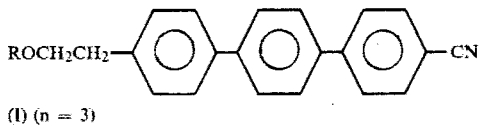
(I) (n = 3)

First, p-phenylphenol (VI) as a starting raw material is subjected to nucleus-hydrogenation reaction to obtain trans-4-phenylcyclohexanol (VII). As the catalyst, platinum group metals such as Pt, Rh, Pd, Re, etc. or Ni catalyst such as Raney nickel may be used, and as the solvent, alcohols, cyclohexane, etc. may be used, but polar solvents are preferable from the viewpoint of the reaction rate. The reaction may be carried out at a reaction temperature of 100° to 200° C. and under a hydrogen pressure of 10 to 100 kg/cm². The compound (VII) is acetylated in a conventional manner to obtain trans-4-phenylcyclohexyl acetate (VIII). This compound (VIII) is then nitrated in the presence of nitric acid to obtain trans-4-(p-nitrophenyl)-cyclohexyl acetate (IX). When this compound (IX) is reduced, nitro group is converted to amino group to obtain trans-4-(p-aminophenyl)-cyclohexyl acetate (X). The reduction may be carried out either with usual nascent hydrogen (e.g. of hydrochloric acid-iron system, hydrochloric acid-tin system or the like) or by hydrogenation reaction under pressure or the atmospheric pressure in the presence of a usual hydrogenation catalyst such as a platinum group metal, nickel, etc. The compound (X) is diazotized in a conventional manner to obtain a diazonium salt of (X) which is then reacted with cuprous bromide in the presence of copper to obtain trans-4-(p-bromophenyl)-cyclohexyl acetate (XI). This compound is hydrolyzed to obtain trans-4-(p-bromophenyl)-cyclohexanol (XII) which is then oxidized with an oxidizing agent such as chromic acid to obtain 4-(p-bromophenyl)-cyclohexanone (XII). This compound (XII) and a 4-brom-1-(β-alkyloxyethyl)-benzene (XIX) are subjected to Grignard reaction to obtain a 1-[p-(β-alkyloxyethyl)-phenyl]-4-(p-bromophenyl)-cyclohexene (XV) which is then subjected to dehydrogenation reaction with sulfur, chloranil or the like to obtain a 4″-(β-alkyloxyethyl)-4-bromoterphenyl (XVI). This compound (XVI) is reacted with cuprous cyanide to obtain an objective 4″-(β-alkyloxyethyl)-4-cyanoterphenyl corresponding to the formula (I) wherein n=3.

The compounds of the formula (I) wherein n=3 can also be produced according to the following steps:

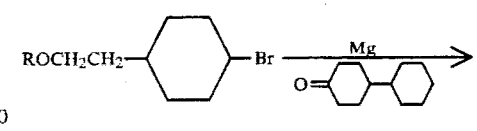
(XIV)         (XVII)

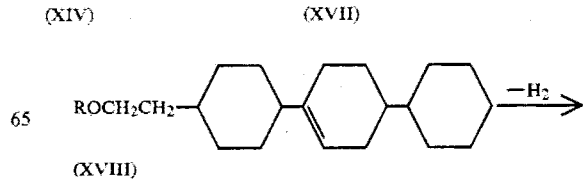
(XVIII)

-continued

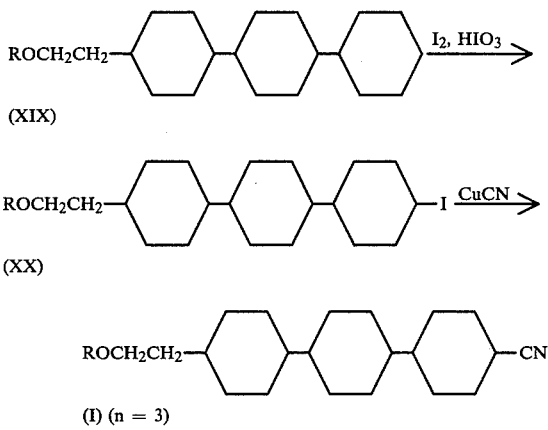

First, 4-phenylcyclohexanone (XVII) is prepared from p-phenylphenol (VI) in the same manner as in the above-mentioned case of 4-(p-bromophenyl) cyclohexanone. The compound (XVII) together with a 4-brom-1-(β-alkyloxyethyl)-benzene (XIV) are subjected to Grignard reaction to obtain a 1-[p-(β-alkyloxyethyl)-phenyl]-4-phenylcyclohexene (XVIII) which is then subjected to dehydrogenation reaction to obtain a 4-(β-alkyloxyethyl)terphenyl (XIX). This compound (XIX) is iodinated with iodine and iodic acid in the same manner as in the case of the compounds of the formula (I) wherein n=2 to obtain a 4''-(β-alkyloxyethyl)-4-iodoterphenyl (XX) which is then subjected to cyanogenation reaction to obtain an objective 4''-(β-alkyloxyethyl)-4-cyanoterphenyl corresponding to the formula (I) wherein n=3.

The compounds of the present invention will be further described in detail by way of Examples (Preparation Examples and Use Examples).

EXAMPLE 1

Preparation of 4'-(β-methyloxyethyl)-4-cyanobiphenyl

Step A

Ethylene glycol monomethyl ether (399 g, 5.245 mols) was dissolved in dry pyridine (1,600 ml) and cooled down to 5° C. or lower. To the solution was added p-toluenesulfonic acid chloride (1,000 g, 5.245 mols) in small amount portions so that the reaction temperature could not exceed 10° C. After completion of the addition, the cooling bath was removed and the mixture was agitated for 4 hours at room temperature, followed by adding 1 l of water and further adding 1 l of toluene.

The resulting mixture was transferred into a separating funnel and the resulting upper toluene layer was washed twice with 6 N—HCl (500 ml, each time) and further washed once with water (500 ml) and furthermore washed four times with water (500 ml, each time), followed by distilling off toluene under reduced pressure to obtain β-methyloxyethyl p-toluenesulfonate (511 g).

Step B

Metallic magnesium (14.6 g, 0.6 mol) was placed in a completely dried 2 l three-neck flask and dry nitrogen gas was passed through the inside of the vessel to completely dry it, followed by adding anhydrous ethyl ether (45 ml) and a trace of iodine. A dry ethyl ether solution (500 ml) of p-bromobiphenyl (140 g, 0.6 mol) was gradually added with stirring while maintaining the reaction temperature at 30° to 35° C., and after the addition, the reaction was further carried out at the same temperature for 3 hours. At an inner temperature of 35° C., an anhydrous ethyl ether solution (300 ml) of β-methyloxyethyl p-toluenesulfonate (276 g, 1.2 mol) obtained in step A was gradually added. During the addition, reflux began to occur due to the reaction heat. After the addition, the mixture was placed under reflux for 2 hours while maintaining it on a water bath at an inner temperature of 35° C. After completion of the reaction, the reaction liquid was cooled and 500 ml of water was added and then 6 N—HCl (1.5 l) was added. The reaction liquid was transferred into a separating funnel and subjected to extraction with toluene (500 ml). The resulting toluene layer was separated from the resulting aqueous layer, and this aqueous layer was further subjected to extraction with toluene (100 ml). The toluene layers were combined together, and insoluble matters therein were removed by suction filtration. The resulting toluene layer was washed once with 2 N—NaOH aqueous solution (200 ml) and filtered through a pleated filter paper, followed by distilling off toluene under reduced pressure. To the residue were added NaOH (10 g), water (20 ml) and ethanol (500 ml), and the mixture was placed under reflux on a water bath for 30 minutes. The mixture liquid was cooled and poured in 1 l of water, and toluene (300 ml) was added, followed by transferring the mixture into a separating funnel, washing the upper toluene layer 3 times with 300 ml of water and distilling off toluene under reduced pressure. The residue was then distilled under reduced pressure and fractions of b.p. 137°~140° C./1.5 mmHg were collected to obtain 4-(β-methyloxyethyl)-biphenyl (IV) (34 g).

Step C

Into a 300 ml three-neck flask were added 4-(β-methyloxyethyl) biphenyl (34 g, 0.16 mol), acetic acid (112 ml), water (30 ml), iodic acid (6.8 g, 0.0384 mol), iodine (17.9 g, 0.0704 mol), carbon tetrachloride (13 ml) and conc. sulfuric acid (4.8 ml). The mixture was warmed by a mantle heater with stirring, and reaction was carried out under reflux at 83° C. for 3 hours. After completion of the reaction, the reaction liquid was cooled down to 70° C., and 10% sodium thiosulfate aqueous solution (10 ml) was added to cause excess iodine to disappear. The liquid was cooled down to room temperature, and the precipitated crystals were recrystallized from ethyl ethanol (300 ml) to obtain 4'-(β-methoxyethyl)-4-iodobiphenyl (V) (30 g) having a melting point of 97°~99.4° C.

Step D

Into a 200 ml three-neck flask were added 4'-(β-methyloxyethyl)-4-iodobiphenyl obtained in Step C (20 g, 0.59 mol), cuprous cyanide (6.2 g, 0.688 mol) and DMF (67 ml), and the mixture was reacted together under reflux with stirring at 149° C. for 6 hours. After completion of the reaction, the reaction liquid was cooled down to room temperature and 29% aqueous ammonia (20 ml) was added, followed by agitation. Toluene (50 ml) and water (100 ml) were then added and the reaction liquid was subjected to suction-filtration. The toluene layer of the filtrate was washed with 6 N-hydrochloric acid and then with sodium hydroxide aqueous solution and further with water till the layer became neutral. The resulting toluene layer was dried with anhydrous sodium sulfate (10 g), and passed through an active alumina layer, followed by distilling off toluene, recrystallizing the residual crystals from methanol (30 ml), filtering and drying to obtain objective 4'-(β-methyloxyethyl)-4-cyanobiphenyl (3 g) having a melting point (C-I point) of 50.7° C. When this product was mixed with 4'-octyloxy-4-cyanobiphenyl and the mixture was subjected to measurement for N→I point, its N→I point through extrapolation was −5° C. (With the above product alone, measurement of N→I point was impossible.) The values of the elemental analysis of the product accorded well with the calculated values thereof as follows:

|   | Analytical values | Calculated values (as $C_{16}H_{15}NO$) |
|---|---|---|
| C | 80.8% | 80.98% |
| H | 6.4% | 6.37% |
| N | 5.8% | 5.90% |

EXAMPLE 2

The step A of Example 1 was repeated except that ethylene glycol monomethyl ether as raw material was replaced by ethylene glycol monoethyl ether, to obtain β-ethyloxyethyl p-toluenesulfonate. Further, the reaction of step B gave 4'-(β-etyloxyethyl) biphenyl which had a boiling point of 132°∼142° C./1.5 mmHg. Next the reaction of step C gave 4'-(β-ethyloxyethyl)-4-iodobiphenyl which had a melting point of 79.5°∼80.5° C. The reaction of step D gave objective 4'-(β-ethyloxyethyl)-4-cyanobiphenyl which had a melting point (C-I point) of 49.4°∼50.6° C. When this product was mixed with 4'-octyloxy-4-cyanobiphenyl and the mixture was subjected to measurement for N→I point, its N→I point obtained through extrapolation was −6° C. The values of the elemental analysis of the product accorded well with its calculated values as follows:

|   | Analytical values | Calculated values (as $C_{17}H_{17}NO$) |
|---|---|---|
| C | 81.1% | 81.24% |
| H | 6.8% | 6.82% |
| N | 5.5% | 5.57% |

The following compounds also were obtained in the same manner as in Examples 1 and 2:
4'-(β-propyloxyethyl)-4-cyanobiphenyl
4'-(β-butyloxyethyl)-4-cyanobiphenyl
4'-(β-pentyloxyethyl)-4-cyanobiphenyl
4'-(β-hexyloxyethyl)-4-cyanobiphenyl
4'-(β-heptyloxyethyl)-4-cyanobiphenyl
4'-(β-octyloxyethyl)-4-cyanobiphenyl
4'-(β-nonyloxyethyl)-4-cyanobiphenyl

EXAMPLE 3

Preparation of 4''-(β-butyloxyethyl)-4-cyanoterphenyl

Step A p-Phenylphenol (VI) (1 kg, 5.88 mols) dissolved in ethanol (2 l) was fed into a 5 l autoclave, and hydrogenation reaction was carried out at a reaction temperature of 150° to 160° C. under a hydrogen pressure of 30 to 40 kg/cm² using a developed Raney nickel (100 g) as catalyst. When 17.6 mols of hydrogen were absorbed, the reaction was stopped. After cooling, the catalyst was filtered off, and the filtrate was concentrated to remove ethanol. The resulting residue was dissolved in toluene. The toluene solution was washed a few times with 2 N—NaOH aqueous solution and further with water, and toluene was then removed by concentration of the solution. The resulting raw crystals were recrystallized from ethanol to obtain trans-4-phenylcyclohexanol (VII) (200 g) having a melting point of 118.4°−119.2° C.

Step B

Trans-4-phenylcyclohexanol (VII) (352.5 g, 2 mols) obtained in Step A, pyridine (791 g) and toluene (200 ml) were mixed and dissolved together, and acetyl chloride (173 g, 2.2 mols) was gradually added at a reaction temperature of 25° C. After the addition, the temperature was raised up to 60° C. to effect the reaction for one hour, followed by cooling. Toluene (300 ml) and water (500 ml) were added and mixed together and the mixture was kept still standing, followed by washing the upper toluene layer twice with 6 N-hydrochloric acid (500 ml, each time), further twice with 2 N—NaOH aqueous solution (500 ml, each time) and furthermore 5 times with water (500 ml, each time). After removal of toluene by concentration of the solution, the resulting residue was recrystallized from a solvent mixture of ethanol (300 ml) and water (50 ml) to obtain trans-4-phenylcyclohexylacetate (VIII) (380 g) having a melting point of 49.0°∼49.7° C.

Step C

Trans-4-phenylcyclohexylacetate (VIII) (380 g, 1.74 mol) obtained in Step B, acetic acid (380 ml) and acetic anhydride (190 ml) were mixed and dissolved together, and an acid mixture of 70% nitric acid (159.7 g, 1.77 mol) and conc. sulfuric acid (900 g) was added at such a rate that the inner temperature did not exceed 20° C., followed by further adding conc. sulfuric acid (300 g) and then reacting them at 30° C. for 4 hours. After completion of the reaction, toluene (1 l) and ice water (1 l) were added while the reaction liquid was cooled by an ice bath, and they were then agitated. The resulting toluene layer was washed three times with water, further with 2 N—NaOH aqueous solution and furthermore with water till the layer became neutral. After removal of toluene by concentration of the layer, the residual raw crystals were recrystallized from ethanol (500 ml) to obtain trans-4-(p-nitrophenyl)-cyclohexylacetate (IX) (267 g) having a melting point of 126.0°∼127.5° C.

Step D

Trans-4-(p-nitrophenyl)-cyclohexylacetate (IX) (267 g, 1.01 mol) obtained in Step C was dissolved in ethyl acetate (1.2 l), and powder of 5% platinum carried on carbon as catalyst (14 g) was added, to allow the solution to absorb hydrogen at 60° C. under the atmospheric pressure. After the absorption of hydrogen stopped, the catalyst was filtered off and the solvent ethyl acetate was removed by concentrating the solution. The resulting raw crystals were recrystallized from ethanol (800 ml) to obtain trans-4-(p-aminophenyl)-cyclohexylacetate (X) (193 g) having a melting point of 132.3°∼134.2° C.

Step E

Trans-4-(p-aminophenyl)-cyclohexylacetate (X) (196 g, 0.84 mol) obtained in Step D was dissolved in acetic acid (390 ml), and 47% hydrobromic acid (361.3 g, 2.10 mols) was added. To the mixture cooled down to 5° C. or lower by an ice bath was gradually added an aqueous solution (78 ml) of sodium nitrite (59.5 g, 0.86 mol) so that the temperature might not exceed 10° C., followed by agitating the mixture at 10° C. or lower for 20 minutes to obtain a diazonium salt of the compound (X). On the other hand, anhydrous copper sulfate (33.4 g, 0.21 mol), copper powder (16.5 g, 0.26 mol), anhydrous sodium bromide (94.8 g, 0.92 mol), conc. sulfuric acid (23.2 g) and water (840 ml) were mixed together, heated and placed under reflux for 3 hours. Under the reflux, a solution of the diazonium salt obtained above was gradually added, and additional reflux was carried out for 2 hours. After cooling, toluene (1,000 ml) was added, and the toluene layer was washed with 6 N-hydrochloric acid, then with 2 N-NaOH aqueous solution and further with water till the layer became neutral, followed by removing toluene by concentration of the layer to obtain a mixture (166.5 g) of trans-4-(p-bromophenyl)-cyclohexylacetate (X1) with trans-4-(p-bromophenyl)-cyclohexanol (X11). This mixture was used, as it was, for the subsequent reaction; however, when the mixture was acetylated in a usual acetylation manner, followed by purification with ethanol, the resulting compound (X1) had a melting point of 77.8°~78.3° C.

Step F

The mixture (208.5 g) of the compound (X1) and the compound (X11) obtained in Step E was dissolved in ethanol (460 ml), and a solution of NaOH (28 g) and water (30 ml) was added and the mixture was heated, followed by reflux for one hour. After cooling, toluene (500 ml) and water (500 ml) were added, and the resulting toluene layer was washed with 2 N—NaOH aqueous solution and further with water till the layer became neutral. After removing toluene by concentration of the layer, the resulting raw crystals were recrystallized from ethyl acetate (130 ml) to obtain trans-4-(p-bromophenyl)-cyclohexanol (X11) (130 g) having a melting point of 109.5°~111.0° C.

Step G

Trans-4-(p-bromophenyl)-cyclohexanol (X11) (130 g, 0.51 mol) obtained in Step F was dissolved in acetone (306 ml), and an oxidizing agent (122 ml) (a solution of anhydrous chromic acid (134 g), conc. sulfuric acid (217 g) and water (250 ml) prepared in advance was gradually added under cooling so that the temperature might not exceed 20° C. After the addition, reaction was further carried out for one hour, followed by adding isopropyl alcohol (60 ml) to reduce the oxidizing agent in excess. Toluene (300 ml) was added and the mixture was agitated. The resulting toluene layer was washed with water to make it neutral. After removing toluene by concentration of the layer, the residue was further subjected to distillation under reduced pressure and fractions of b.p. 135°~145° C./2 mmHg were collected and recrystallized from a solvent mixture of hexane (70 ml) and ethanol (5 ml) to obtain 4-(p-bromophenyl)-cyclohexanone (X111) (71.8 g) having a melting point of 59.4°~61.4° C.

Step H

Metallic magnesium (6.9 g, 0.28 mol) was introduced into a completely dried 1 l three-neck flask and the inside of the vessel was completely dried by passing dry nitrogen gas through it, followed by adding anhydrous tetrahydrofuran (50 ml) and a trace of iodine. An anhydrous tetrahydrofuran solution (146 ml) of 4-brom-1-($\beta$-butyloxyethyl)-benzene (X1V) (73 g, 0.28 mol) was gradually added with stirring, while the temperature was maintained at 30°~35° C., followed by further reaction at the same temperature for 1.5 hour. The reaction liquid was ice-cooled to reduce the inner temperature down to 5° C. or lower, followed by adding an anhydrous tetrahydrofuran solution (146 ml) of 4-(p-bromophenyl)-cyclohexanone (X111) (72 g, 0.28 mol) obtained in Step G, at such a rate that the inner temperature did not exceed 10° C. After reaction at room temperature for 30 minutes, a small amount of N—HCl was added to make the contents weakly acidic followed by adding toluene (200 ml), separating the toluene layer from the aqueous layer, subjecting the aqueous layer to extraction with toluene (50 ml), combining the toluene layers together, washing the combined layers with water and removing toluene by concentration of the layers. To the resulting residue were added toluene (200 ml) and potassium hydrogen sulfate (10 g) and the mixture was heated and placed under reflux at 110° C. for one hour. After cooling, the toluene solution was washed with water to make it neutral followed by removing toluene by concentration of the solution. The resulting raw crystals were recrystallized from ethanol (200 ml) to obtain 1-[p-($\beta$-butyloxyethyl)-phenyl]-4-(p-bromophenyl)-cyclohexene (XV) (57.5 g) having a melting point of 86.5°~89.5° C.

Step I

A mixture of 1-[p-($\beta$-butyloxyethyl)-phenyl]-4-(p-bromophenyl)-cyclohexene (XV) (55 g, 0.13 mol) obtained in Step H, chloranil (78.4 g, 0.32 mol) and xylene (624 ml) was heated and placed under reflux for 24 hours. After cooling, toluene (800 ml) was added, insoluble solid filtered off and toluene removed by concentrating the filtrate. The resulting raw crystals were recrystallized from ethyl acetate (50 ml) to obtain 4"-($\beta$-butyloxyethyl)-4-bromoterphenyl (XV1) (29 g) having a melting point of 225.7°~227.0° C.

Step J

A mixture of 4"-($\beta$-butyloxyethyl)-4-bromoterphenyl (XV1) (29 g, 0.071 mol) obtained in Step I, N-methyl-2-pyrolidone (70 ml) and cuprous cyanide (7.6 g) was heated and placed under reflux for 4 hours. After cooling down to 60° C., a 7.8% aqueous solution of ferric chloride (107 ml) was added and the mixture was then cooled down to room temperature, followed by adding toluene (150 ml) and stirring.

The resulting toluene layer was washed with 6 N hydrochloric acid, then with 2 N—NaOH aqueous solution and further with water till the layer became neutral, and water contained in the toluene layer was removed by azeotropic distillation, followed by passing the layer through an alumina-packed column to remove a trace of impurities by adsorption. Toluene was removed by concentration of the layer. The resulting crystals were recrystallized from ethyl acetate to obtain objective 4"-($\beta$-butyloxyethyl)-4-cyanoterphenyl (I) (13.4 g). This substance was a nematic liquid-crystalline compound and had a melting point (C-N point) of 89.0° C. and a transparent point (N-I point) of 184.5° C. The values of the elemental analysis of the compound accorded well with its calculated values as follows:

|   | Analytical values | Calculated value (as $C_{25}H_{25}NO$) |
| --- | --- | --- |
| C | 84.1% | 84.47% |
| H | 7.2% | 7.09% |
| N | 3.8% | 3.94% |

EXAMPLES 4 AND 5

Example 3 was repeated except that 4-brom-1-($\beta$-butyloxyethyl)-benzene used in Step H of Example 3 was replaced by 4-brom-1-($\beta$-ethyloxyethyl)benzene or 4-brom-1-($\beta$-propyloxyethyl)-benzene, to obtain 4"-($\beta$- yloxyethyl)-4-cyanoterphenyl (Example 4) and 4''--propyloxyethyl)-4-cyanoterphenyl (Example 5), re-ectively. Their values of physical properties are own in Table 1 together with those of Example 3.

TABLE 1

| Example | R in formula (I) | Phase transition point (°C.) | |
|---|---|---|---|
| | | C-N point | N-I point |
| 4 | $C_2H_5$ | 120 | 215 |
| 5 | $C_3H_7$ | 99.5 | 193.5 |
| 3 | $C_4H_9$ | 89 | 184.5 |

The following compounds could be obtained in the me manner as above:

4''-($\beta$-methyloxyethyl)-4-cyanoterphenyl,
4''-($\beta$-pentyloxyethyl)-4-cyanoterphenyl,
4''-($\beta$-hexyloxyethyl)-4-cyanoterphenyl,
4''-($\beta$-heptyloxyethyl)-4-cyanoterphenyl,
4''-($\beta$-octyloxyethyl)-4-cyanoterphenyl,
4''-($\beta$-nonyloxyethyl)-4-cyanoterphenyl, and compounds having a branched alkyl group.

EXAMPLE 6

(Use Example 1)

A liquid crystal composition consisting of

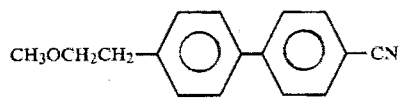

| | |
|---|---|
| $H_7$—⟨H⟩—⟨○⟩—CN | 24 parts by weight, |
| $H_{11}$—⟨H⟩—⟨○⟩—CN | 36 parts by weight, |
| $H_{15}$—⟨H⟩—⟨○⟩—CN | 25 parts by weight, and |
| $H_{11}$—⟨H⟩—⟨○⟩—⟨○⟩—CN | 15 parts by weight | d a nematic liquid crystal temperature range (MR) of 10° ~ +72.3° C., a viscosity at 20° C., $\eta_{20}$ of 28.8 cp d a dielectric anisotropy $\Delta\epsilon$ of 11.1 ($\epsilon_{||}$=15.5; _=4.4), and when this composition was sealed in a TN ll having a cell thickness of 10 $\mu$m, and its threshold ltage and saturation voltage were measured, the val-s were 1.72 V and 2.5 V, respectively.

To 80 parts by weight of this composition were added  parts by weight of

CH$_3$OCH$_2$CH$_2$—⟨○⟩—⟨○⟩—CN hich was one of the compounds of the present inven-n. The resulting liquid crystal composition had a MR ' −15° ~ +57.4° C., a viscosity $\eta_{20}$ of 33.3 cp and a $\Delta\epsilon$ ' 12.8 ($\epsilon_{||}$ =18; $\epsilon\perp$=5.2), and when it was sealed in the me cell as above, the threshold voltage and saturation ltage measured were much reduced down to 1.37 V d 1.95 V, respectively.

EXAMPLE 7

(Use Example 2)

A liquid crystal composition consisting of

| | |
|---|---|
| $C_5H_{11}$—⟨○⟩—⟨○⟩—CN | 45 parts by weight |
| $C_7H_{15}$—⟨○⟩—⟨○⟩—CN | 29 parts by weight, |
| $C_8H_{17}O$—⟨○⟩—⟨○⟩—CN | 15 parts by weight, and |
| $C_5H_{11}$—⟨○⟩—⟨○⟩—⟨○⟩—CN | 11 parts by weight, | had a nematic liquid crystal temperature range (MR) of −10° ~ +63.3° C., a viscosity at 20° C., $\eta_{20}$ of 45.3 cp and a dielectric anisotropy $\Delta\epsilon$ of 12.4 ($\epsilon_{||}$=17.2; $\epsilon\perp$=4.8), and when the composition was sealed in a TN cell having a cell thickness of 10 $\mu$m and the threshold voltage and saturation voltage were measured, the values were 1.55 V and 2.2 V, respectively.

To 80 parts by weight of this composition was added 20 parts by weight of

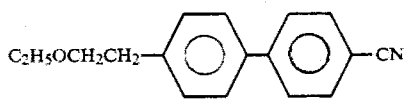

$C_2H_5OCH_2CH_2$—⟨○⟩—⟨○⟩—CN which was one of the compounds of the present invention. The resulting liquid crystal composition had a MR of −15° ~ +49.0° C., a $\eta_{20}$ of 47.5 cp and a $\Delta\epsilon$ of 13.3 ($\epsilon_{||}$=19.1; $\epsilon\perp$=5.8), and when it was sealed in the same cell as above, its threshold voltage and saturation voltage measured were much reduced down to 1.23 V and 1.76 V, respectively.

EXAMPLE 8

(Use Example 3)

A liquid crystal composition consisting of

| | |
|---|---|
| $C_3H_7$—⟨H⟩—COO—⟨○⟩—OC$_4$H$_9$ | 20 parts by weight, |
| $C_4H_9$—⟨H⟩—COO—⟨○⟩—OC$_2$H$_5$ | 20 parts by weight, |
| $C_5H_{11}$—⟨H⟩—COO—⟨○⟩—OCH$_3$ | 20 parts by weight, and |
| $CH_3O$—⟨○⟩—COO—⟨○⟩—C$_5$H$_{11}$ | 20 parts by weight | had a negative dielectric anisotropy ($\Delta\epsilon$: about-1), and with this composition alone, display in a TN cell was impossible.

Whereas when

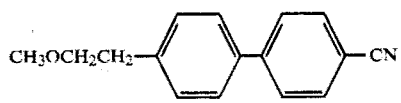

CH$_3$OCH$_2$CH$_2$—⟨○⟩—⟨○⟩—CN of Example 1 of the present invention (20 parts by weight) was added to the above composition, the resulting composition had the following properties and characteristic properties, and display in a TN cell became possible:

| | |
|---|---|
| Transparent point | 50.1° C. |
| Δε | 2.7 (ε∥ = 8.1; ε⊥ = 5.4) |
| Threshold voltage | 1.98V |
| Saturation voltage | 2.70V |

EXAMPLE 9

(Use Example 4)

A liquid crystal composition consisting of

| | |
|---|---|
| C$_5$H$_{11}$—⟨O⟩—⟨O⟩—CN | 43 parts by weight, |
| C$_7$H$_{15}$—⟨O⟩—⟨O⟩—CN | 27 parts by weight, |
| C$_8$H$_{17}$—⟨O⟩—⟨O⟩—CN | 15 parts by weight, and |
| C$_4$H$_9$OC$_2$H$_4$—⟨O⟩—⟨O⟩—⟨O⟩—CN | 15 parts by weight |

(Compounds of Example 3)

had a transparent point (N-I point of 62.5° C., a dielectric anisotropy Δε of 12.0 and an optical anisotropy Δn of 0.22. The compounds of this composition were well dissolved in one another, and even when the composition was subjected to a heat cycle test between −30° C. and +25° C. for 200 hours, no deposition of crystal was observed. This liquid crystal composition was sealed in a TN cell having a cell thickness of 10 μm, prepared by vacuum-depositing silicon oxide onto a glass base having transparent electrodes applied thereonto, followed by a parallel orientation treatment by means of rubbing treatment, and its threshold voltage and saturation voltage were measured. The values were 1.46 V and 2.02 V, respectively. A liquid crystal composition wherein

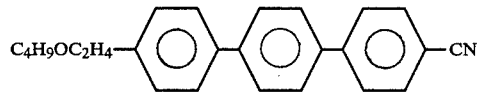

(a compound of the present invention) was excluded from the above liquid crystal composition, had a N-I point of 45.8° C., a Δε of 1.7 and a Δn of 0.20. Thus it can be seen that the transparent points (both Δε and Δn) were raised due to the compound of the present invention. When this liquid crystal composition was sealed in the same TN cell as above and the threshold voltage and saturation voltage were measured, the values were 1.31 V and 1.84 V, respectively.

What is claimed is:

1. A compound expressed by the formula

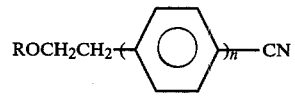

wherein R represents an alkyl group of 1 to 9 carbon atoms and n represents 2 or 3.

2. A compound according to claim 1, expressed by the formula

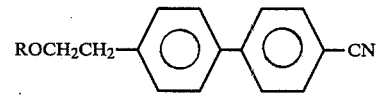

wherein R represents an alkyl group of 1 or 2 carbon atoms.

3. A compound according to claim 1, expressed by the formula

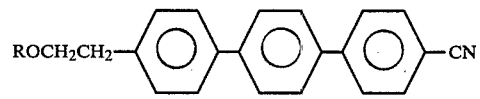

wherein R represents an alkyl group of 2 to 4 carbon atoms.

4. A process for producing a compound according to claim 1 or claim 2 which comprises the steps of iodinating a 4-(β-alkyloxyethyl)biphenyl to obtain a 4′-(β-alkyloxyethyl)-4-iodobiphenyl which is then cyanogenated with cuprous cyanide to obtain a 4′-(β-alkyloxyethyl)-4-cyanobiphenyl.

5. A process according to claim 4, wherein the cyanogenation reaction is carried out at a temperature not higher than 149° C.

6. A liquid crystal composition comprising a mixture of compounds, at least one of which is a compound expressed by the formula

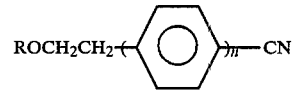

wherein R represents an alkyl group of 1 to 9 carbon atoms and n represents 2 or 3.

* * * * *